United States Patent
Heaton et al.

(10) Patent No.: US 10,307,518 B2
(45) Date of Patent: Jun. 4, 2019

(54) SYSTEMS AND METHODS FOR IMPROVED CONNECTION TO WOUND DRESSINGS IN CONJUNCTION WITH REDUCED PRESSURE WOUND TREATMENT SYSTEMS

(71) Applicant: KCI Licensing, Inc., San Antonio, TX (US)

(72) Inventors: Keith Patrick Heaton, Poole (GB); Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 288 days.

(21) Appl. No.: 15/247,566

(22) Filed: Aug. 25, 2016

(65) Prior Publication Data

US 2016/0361475 A1    Dec. 15, 2016

Related U.S. Application Data

(60) Division of application No. 14/579,664, filed on Dec. 22, 2014, now Pat. No. 9,452,246, which is a
(Continued)

(51) Int. Cl.
*A61M 1/00* (2006.01)
*A61F 13/00* (2006.01)

(52) U.S. Cl.
CPC ..... *A61M 1/0035* (2014.02); *A61F 13/00068* (2013.01); *A61M 1/0025* (2014.02);
(Continued)

(58) Field of Classification Search
CPC ........ A61M 1/0031; A61M 2205/3344; A61M 1/0025; A61M 25/0026; A61M 2025/0003; A61M 2039/082; A61M 2025/0026
(Continued)

(56) References Cited

U.S. PATENT DOCUMENTS 1,355,846 A    10/1920   Rannells
2,547,758 A     4/1951   Keeling
(Continued)

FOREIGN PATENT DOCUMENTS

AU    550575 B2    3/1986
AU    745271 B2    3/2002
(Continued)

OTHER PUBLICATIONS

Brazilian Unfavorable Technical Opinion for corresponding Application No. PI0706893-0, mailed Jun. 25, 2018.
(Continued)

*Primary Examiner* — Susan S Su (57) ABSTRACT

A system for applying reduced pressure to tissue includes a multi-lumen reduced pressure delivery tube having a proximate end, a distal end, a primary lumen extending through the conduit from the proximate end to the distal end, and an ancillary lumen extending through the conduit from the proximate end to the distal end. A vacuum pump is coupled to the proximate end of the primary lumen, and a reduced pressure adapter is coupled to the distal end of the reduced pressure delivery tube. The adapter includes channels to direct liquid away from the ancillary lumens and into the primary lumen.

6 Claims, 7 Drawing Sheets

Related U.S. Application Data continuation of application No. 13/651,284, filed on Oct. 12, 2012, now Pat. No. 8,951,236, which is a division of application No. 12/650,316, filed on Dec. 30, 2009, now Pat. No. 8,308,703, which is a division of application No. 11/702,822, filed on Feb. 6, 2007, now Pat. No. 7,651,484.

(60) Provisional application No. 60/765,548, filed on Feb. 6, 2006.

(52) U.S. Cl.
CPC ........ A61M 1/0031 (2013.01); A61M 1/0086 (2014.02); A61M 1/0088 (2013.01); A61M 1/0037 (2013.01); A61M 1/0092 (2014.02); A61M 2205/3344 (2013.01); A61M 2205/584 (2013.01)

(58) Field of Classification Search
USPC ........................................ 604/304, 305, 326
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,460,368 A | 7/1984 | Allison et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,013,300 A | 5/1991 | Williams |
| 5,034,006 A | 7/1991 | Hosoda et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,879,499 A | 3/1999 | Corvi |
| 6,071,267 A | 6/2000 | Zamierowski |
| 6,135,116 A | 10/2000 | Vogel et al. |
| 6,142,982 A | 11/2000 | Hunt et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,004,915 B2 | 2/2006 | Boynton et al. |
| 7,195,624 B2 | 3/2007 | Lockwood et al. |
| 7,276,051 B1 | 10/2007 | Henley et al. |
| 7,485,112 B2 | 2/2009 | Karpowicz et al. |
| 7,678,102 B1 | 3/2010 | Heaton |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,690,845 B2 | 4/2014 | Long et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |

(56) References Cited

U.S. PATENT DOCUMENTS

| | | | |
|---|---|---|---|
| 2002/0115951 | A1 | 8/2002 | Norstrem et al. |
| 2002/0115952 | A1 | 8/2002 | Johnson et al. |
| 2002/0120185 | A1 | 8/2002 | Johnson |
| 2002/0143286 | A1 | 10/2002 | Tumey |
| 2005/0004534 | A1 | 1/2005 | Lockwood et al. |
| 2009/0012501 | A1 | 1/2009 | Boehringer et al. |
| 2010/0298792 | A1 | 11/2010 | Weston et al. |
| 2011/0282310 | A1 | 11/2011 | Boehringer et al. |
| 2013/0304001 | A1 | 11/2013 | Livne et al. |
| 2014/0163491 | A1 | 6/2014 | Schuessler et al. |
| 2014/0207027 | A1 | 7/2014 | Navia et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 10039196 C2 | 11/2002 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 03057070 A2 | 7/2003 |
| WO | 2004037334 A1 | 5/2004 |
| WO | 2009/070905 A1 | 6/2009 |
| WO | 2009071935 A1 | 6/2009 |

OTHER PUBLICATIONS

Extended European Search Report for corresponding Application No. 181586926, dated Jun. 18, 2018.

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., MD., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

(56) References Cited

OTHER PUBLICATIONS

M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
European Search Report for corresponding European Application No. 07763367.6 dated Jan. 4, 2013.

SYSTEMS AND METHODS FOR IMPROVED CONNECTION TO WOUND DRESSINGS IN CONJUNCTION WITH REDUCED PRESSURE WOUND TREATMENT SYSTEMS

CROSS-REFERENCE TO RELATED APPLICATIONS

This application is a divisional of U.S. patent application Ser. No. 14/579,664, filed Dec. 22, 2014, which is a continuation application of U.S. patent application Ser. No. 13/651,284, filed Oct. 12, 2012, now U.S. Pat. No. 8,951,236, which is a divisional application of U.S. patent application Ser. No. 12/650,316, filed Dec. 30, 2009, now U.S. Pat. No. 8,308,703, which is a divisional of U.S. patent application Ser. No. 11/702,822, filed Feb. 6, 2007, now U.S. Pat. No. 7,651,484, which claims the benefit of U.S. Provisional Application No. 60/765,548, filed Feb. 6, 2006, all of which are hereby incorporated by reference.

BACKGROUND OF THE INVENTION

1. Field of the Invention

The present invention relates to generally to systems and methods for providing reduced pressure treatment to tissue, particularly open wounds. The present invention relates more specifically to systems and methods for improving the connection between a tissue dressing and reduced pressure source instrumentation used in conjunction with reduced pressure wound treatment (RPWT).

2. Description of the Related Art

Various therapies have been developed over time to facilitate the process of wound closure and healing. Wound closure generally involves the inward migration of epithelial and subcutaneous tissue adjacent the wound. This migration is ordinarily assisted by the inflammatory process, whereby blood flow is increased and various functional cell types are activated. As a result of the inflammatory process, blood flow through damaged or broken vessels is stopped by capillary level occlusion, whereafter cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but are also less able to successfully fight bacterial infection and, thus, less able to naturally close the wound. Additionally, some wounds harden and inflame to such a degree that closure by stapling or suturing is not feasible. Examples of wounds not readily treatable with staples or suturing include large, deep, open wounds; decubitus ulcers; ulcers resulting from chronic osteomyelitis; and partial thickness burns that subsequently develop into full thickness burns.

As a result of the shortcomings of mechanical wound closure devices, methods and apparatus for draining wounds by applying continuous and/or periodic reduced pressures have been developed. When applied over a sufficient area of the wound, such reduced pressures have been found to promote the migration of epithelial and subcutaneous tissues toward the wound. In practice, the application to a wound of reduced pressure typically involves the mechanical-like contraction of the wound with simultaneous removal of excess fluid. In this manner, RPWT augments the body's natural inflammatory process while alleviating many of the known intrinsic side effects, such as the production of edema caused by increased blood flow absent the necessary vascular structure for proper venous return.

Vacuum or reduced pressure induced healing of open wounds has recently been popularized by Kinetic Concepts, Inc. of San Antonio, Tex., through its commercially available RPWT systems product line. The reduced pressure induced healing process has been described in commonly assigned U.S. Pat. No. 4,969,880, issued on Nov. 13, 1990 to Zamierowski, as well as in its related patents, including U.S. Pat. No. 5,100,396, issued on Mar. 31, 1992; U.S. Pat. No. 5,261,893, issued on Nov. 16, 1993; and U.S. Pat. No. 5,527,293 issued Jun. 18, 1996, the disclosures of which are each incorporated herein by reference. Further improvements and modifications of the RPWT process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are each incorporated by reference as though fully set forth herein. Additional improvements have also been described in U.S. Pat. No. 6,142,982, issued on May 13, 1998 to Hunt, et al.

One important component of a RPWT system is the device or structure that connects the reduced pressure source (a vacuum pump, typically) to the components (a granular foam layer, typically) enclosed within the pad or wound dressing. This reduced pressure port structure must adhere to the wound dressing and be in fluid communication with the foam layer of the dressing. The port is preferably of low profile, in the nature of an attachment pad, in order to provide both comfort and safety to the patient. Various efforts have been made in the past to provide suitable adapter configurations to effectively connect the reduced pressure source (through tubing, typically) to a tissue site.

Commensurate with the application of continuous and/or periodic reduced pressures to a wound is a coordinated monitoring of the pressure present at the tissue site as a result of the application of the RPWT system. It has become important, therefore, to provide systems that are capable of monitoring and responding to changes in the level of reduced pressure applied at the tissue site. Various regimens of RPWT that involve cycling the reduced pressure applied to the wound have been found to be beneficial under certain circumstances. Other situations benefit from a constant but closely regulated application of reduced pressure. In any case, it becomes valuable to accurately monitor the level of reduced pressure applied at the tissue site.

Generally it is not possible to characterize the pressure level at the tissue site by simply measuring the level of reduced pressure that the reduced pressure source is providing, either at the source or in the conduit lines connecting the source to the wound dressing. Fluid flow within the primary lumen of tubing associated with RPWT systems prevents using pressure level measurements at the instrumentation from being accurate indicators of the level or stability of the pressure at the tissue site itself. Other methods for directly monitoring the wound pressure levels are therefore required.

Some efforts have been made in the past to provide a separate pressure sensing or measurement conduit to the wound site connected to monitoring instrumentation. These efforts have typically provided a separate lumen within the RPWT tubing or have utilized a separate section of tubing altogether. The assumption being made with such systems, however, is that the ancillary measurement lumen or measurement tube is open and clear down to its port at the wound dressing. This is not always a valid assumption as, despite the fact that the measurement lumen is not forcibly drawing fluids in as is being done in the primary flow lumen of the RPWT system, it still collects fluids and other materials that inhibit or altogether block its function. The typically smaller cross-section of such measurement lumens may reduce the port size, and therefore the chance of fluid or other matter entering the port, but the same smaller cross-section results in even minor blockages becoming significant.

SUMMARY OF THE INVENTION

Exemplary embodiments of the present invention provide improvements to the structure and use of the connector elements between the wound dressing and the reduced pressure source in a reduced pressure wound treatment (RPWT) system. More specifically certain exemplary embodiments provide:

(A) A low profile reduced pressure adapter that improves the reliability of operation and prevents or reduces instances of unintentional fluid ingress into measurement lumens;

(B) An improved reduced pressure delivery tube comprising an oval tubing structure with a larger inner lumen and smaller outer lumens for supporting the dynamic pressure functionality described below;

(C) An improved and dynamic method of measuring wound pressure that overcomes certain problems with existing pressure control in RPWT systems;

(D) An improved reduced pressure adapter structure having rotational functionality to facilitate the comfort of the attachment to the patient; and (E) A structure to provide indications of the presence of bacteria within the reduced pressure adapter and fluids transported therethrough.

The improved reduced pressure adapter includes a conduit housing with a primary conduit and at least one secondary conduit for fluid connection to a wound dressing. The reduced pressure adapter also may include a base with a substantially circular shape. The conduit housing includes a recessed region defining an entry surface. The primary conduit connects the entry surface to a primary lumen of a multi-lumen reduced pressure delivery tube, and ancillary conduits connect the entry surface to ancillary lumens of the multi-lumen reduced pressure delivery tube. Channels positioned on the entry surface preferentially route liquids and other fluids into the primary conduit in order to prevent the clogging of the ancillary conduits, which are generally utilized to measure pressure within the wound dressing.

The improved reduced pressure delivery tube incorporates a larger primary inner lumen to effect the conduction of reduced pressure to the tissue and fluids away from the tissue. Smaller outer ancillary lumens are provided to support the hereinafter described dynamic pressure functionality that insures the continuity of accurate pressure measurements through the monitoring of the open or closed (clogged) state of each of the ancillary lumens. The reduced pressure delivery tube may be mated to the improved reduced pressure adapter described above, or may be used with other adapters to fluidly connect a reduced pressure source and pressure sensors to a porous pad or other distribution manifold.

The improved method of measuring pressure addresses certain problems with existing pressure control in RPWT systems that result from excessive fluid incursion into the measurement lumens of the system. Each of the ancillary lumens are monitored for their responsiveness to changes in the reduced pressure source (and thus in the wound dressing itself). A slow response in one of the ancillary lumens is indicative of clogging in that lumen, and as a result, the RPWT system considers the pressure measurement from the clear ancillary lumen as the accurate measurement. The system further allows for the introduction of elevated pressure into the clogged lumen in a manner that may serve to clear the lumen of fluid obstruction, all the while the second of the two ancillary lumens may continue to function as a monitoring channel for measuring the pressure at the tissue site.

In other embodiments the improved reduced pressure adapter structure incorporates rotational functionality to improve the patient's convenience and comfort. The conduit housing is positioned on and rotatably attached to the perimeter base in a manner that allows the reduced pressure adapter and attached tubing to rotate with respect to the wound dressing thereby reducing strain on the dressing and the reduced pressure adapter.

Finally, in yet further embodiments, the improved reduced pressure adapter incorporates an internal surface, preferably formed on the interior perimeter wall of the conduit housing of the adapter, to provide indications of the presence of bacteria within the adapter enclosure and therefore the fluids transported through the adapter. This indicator surface retains a layer of material sensitive to the volatile organic compounds (VOC) associated with various targeted microorganisms. The VOC sensitive surface develops a specific color pattern depending on the type of VOC and therefore the type of microorganism present. The color pattern may be visually discerned through the clear material of the reduced pressure adapter construction or may be automatically detected by photometric color analysis using one of a variety of such photometric sensor devices.

Finally, many other features, objects, and advantages of the present invention will be apparent to those of ordinary skill in the relevant arts, especially in light of the foregoing discussions and the following drawings and exemplary detailed description.

BRIEF DESCRIPTION OF THE DRAWINGS

Although the scope of the present invention is much broader than any particular embodiment, a detailed description of the preferred embodiment follows, together with illustrative figures, wherein like reference numerals refer to like components, and wherein.

DETAILED DESCRIPTION OF PREFERRED EMBODIMENTS

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Reduced Pressure Adapter

Improvements in an RPWT system are disclosed that provide a reduced pressure adapter to improve the reliability of operation and prevent or reduce instances of unintentional liquid ingress into the measurement lumens of a reduced pressure delivery tube, particularly in conjunction with a low-profile dressing. Traditional adapters typically include both a sensing lumen and a reduced pressure delivery lumen together an elbow-shaped housing. A common cause of failure for these reduced pressure adapters results from liquid ingress into the sensing lumen, which may cause the control of therapy to become unstable and, in extreme cases, may contribute to the eventual shutdown of the device. Part of this problem is due to the location of the fluid conduction and the nature of wound fluid in general. Wound excretions and fluids are generally pseudoplastic in consistency and will splash and foam in the elbow of a reduced pressure apparatus under the influence of reduced pressure. One goal of certain exemplary embodiments of the present invention, therefore, is to prevent the wound liquids and other non-gaseous fluids from entering the sensing lumen.

One concept of the improved reduced pressure adapter is for the lumens to be separate down to the distribution manifold of the wound dressing so that the distribution manifold becomes the barrier between the sensing lumens and the reduced pressure path. The underside of the reduced pressure adapter is provided with channel features that attract small droplets splashed inside the reduced pressure adapter during periods of high flow or after a large slug of liquid has been pulled into the tubing. This preferencing of the liquid and solid matter into the larger primary lumen, and away from the smaller ancillary measurement lumens, helps prevent the lumens from becoming blocked. The concept further includes providing offset outer measurement lumen ports in the pad, which are designed such that in most orientations one of the two should be above the flow level in the distribution manifold of the dressing. The reduced pressure adapter is further intended to operate in conjunction with the dynamic pressure control methodologies described in more detail below. The reduced pressure adapter may also include an adhesive drape or cover that secures the reduced pressure adapter within the wound. The profile of the reduced pressure adapter is low for increased patient comfort, and the reduced pressure adapter is preferably elbow-shaped such that the connecting tubing is routed cleanly away from the tissue site.

Figure 1:
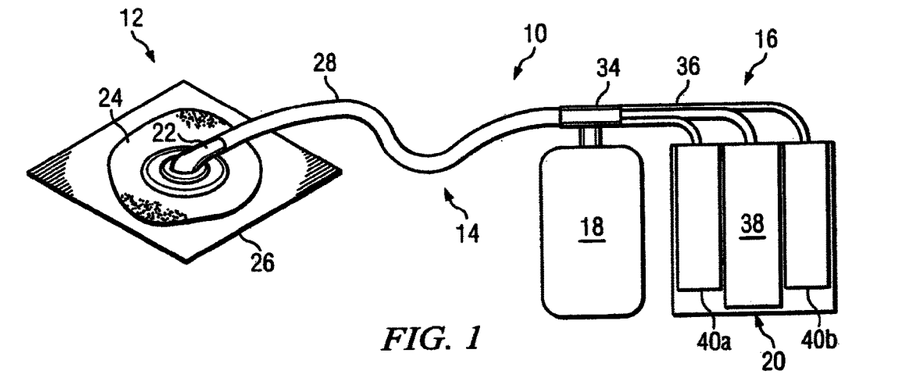
FIG. 1 is a partially schematic, perspective view of the general arrangement of the components of a reduced pressure wound treatment (RPWT) system incorporating the improved elements of an exemplary embodiment of the present invention.

Reference is made first to FIG. 1 for a general description of the components included in a reduced pressure wound treatment (RPWT) system incorporating the improved elements of an exemplary embodiment of the present invention. The three primary components of RPWT system 10 include wound dressing 12, reduced pressure delivery tube 14, and remote fluid containment and instrumentation 16.

Wound dressing 12 is generally comprised of a distribution manifold 24 such as a porous pad or granular foam and a cover or drape 26 that secures the distribution manifold at a tissue site. Dressing 12 also may include improved reduced pressure adapter 22, as shown positioned on distribution manifold 24 and adhered thereto by an adhesive positioned on the reduced pressure adapter 22, the wound drape 26, or a separate adhesive drape associated with reduced pressure adapter 22.

Reduced pressure delivery tube 14 is a multi-lumen tube, comprised of one or more tubing sections 28 which, as an assembled structure, provide a continuous conduit between reduced pressure adapter 22 and container connector 34 positioned on fluid container 18. As described in more detail below, and as known in the art, liquid and other exudates drawn by RPWT system 10 are removed from the tubing at this point and are retained within container 18. Sections of additional tubing in the form of instrumentation tubing 36*a* and 36*b* likewise extend from container connector 34 to instrumentation components 20. In certain embodiments of the present invention, instrumentation components 20 comprise a reduced pressure source 38 and pressure monitoring instrument components 40*a* and 40*b*. Described in more detail below, each of these three instrument components 20 is individually associated with one of three isolated conduits (tubes or lumens) that extend from reduced pressure adapter 22 into remote fluid containment and instrumentation 16.

Figure 2:
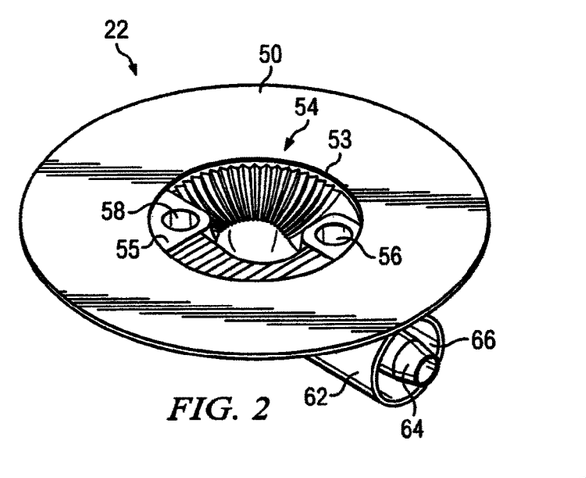
FIG. 2 is a perspective view of the underside (open side) of an improved reduced pressure adapter according to an embodiment of the present invention.

Reference is now made to FIGS. 2-9 for a more detailed description of the reduced pressure adapter 22. FIG. 2 provides a perspective view of the underside of reduced pressure adapter 22 showing the various structural elements within the opening of reduced pressure adapter 22 that are adapted to contact the distribution manifold 24 (not shown) of the wound dressing.

Reduced pressure adapter 22 generally comprises a base 50, which may be adhered to the distribution manifold, and a conduit housing 62 coupled to the base 50. Conduit housing 62 includes a primary conduit and a pair of ancillary conduits. The base 50 includes an aperture 53, which is positioned over the distribution manifold and through which the liquids and gases (collectively referred to as "fluids") are drawn from the tissue site. A significant feature of improved reduced pressure adapter 22 is the presence of channel elements positioned near and in fluid communication with aperture 53 and the effective way in which the channel elements direct liquid into the primary conduit for drainage. The routing of liquids into the primary conduit maintains the ancillary conduits of the system open for pressure measurement purposes.

Referring to FIG. 2, the conduit housing 62 of reduced pressure adapter 22 includes a recessed region 54 defining an entry surface 55. The primary conduit terminates on the entry surface 55 at a primary port 60, which is centrally located at an apex of the recessed region 54. The ancillary conduits terminate on the entry surface 55 at ancillary ports 56 and 58. The ancillary ports are positioned near diametrically opposing edges of aperture 53.

A second end of the primary conduit terminates at a primary lumen interface 64. Primary lumen interface 64 is generally centrally positioned within aperture 66. Ancillary lumen interfaces 48, 49 (see FIG. 5) to the ancillary conduits also are located within aperture 66 and are described in more detail below.

Figure 3:
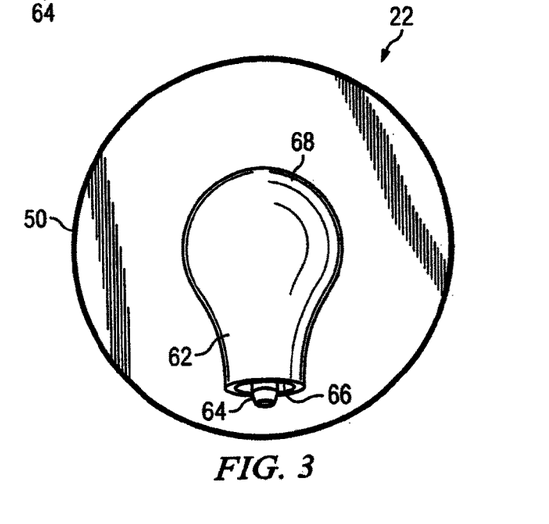
FIG. 3 is a plan view of the topside (closed side) of the improved reduced pressure adapter of FIG. 2.

FIG. 3 provides a plan view (from above) of reduced pressure adapter 22. The conduit housing 62 is preferably "elbow" shaped; however, the conduit housing may be configured at any desired angle or may extend perpendicularly from base 50. In the elbow configuration illustrated in FIG. 3, reduced pressure adapter 22 is seen to comprise base 50 and a centrally positioned conduit housing 62. Conduit housing 62 includes an elbow region 68, and the conduit housing 62 internally comprises conduits between the ports 56, 58, 60 and the ancillary and primary lumen interfaces 48, 49, 64.

Figure 4:
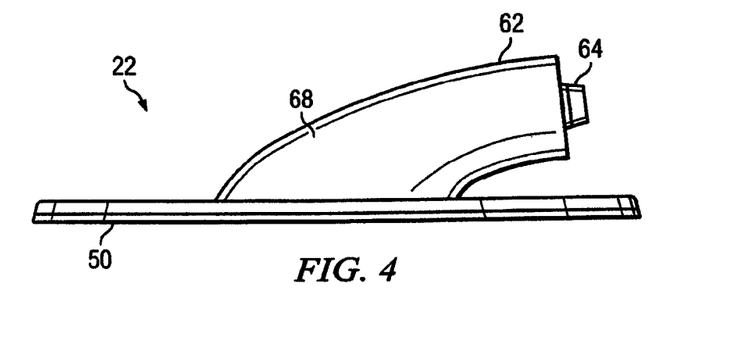
FIG. 4 is a first side view of the improved reduced pressure adapter of FIG. 2.
Figure 5:
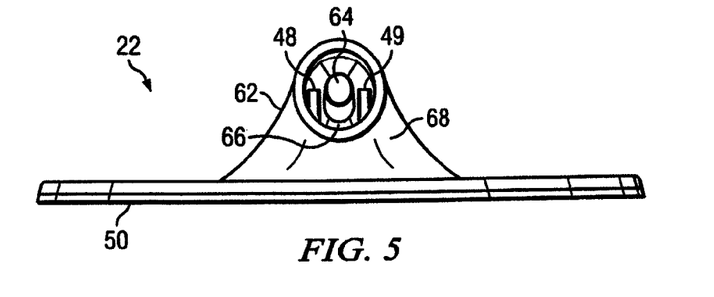
FIG. 5 is an end view of the improved reduced pressure adapter of FIG. 2.
Figure 6:
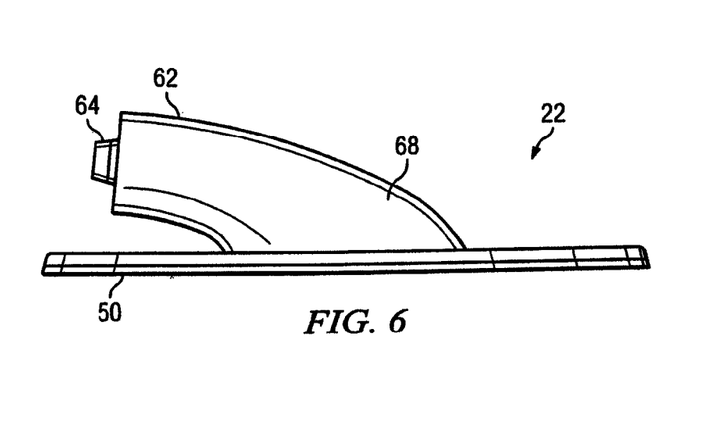
FIG. 6 is a second side view of the improved reduced pressure adapter of FIG. 2.

FIGS. 4, 5 & 6 show side, and end views of the reduced pressure adapter 22. Reduced pressure adapter 22, as seen in the side view shown in FIG. 4, is of low profile construction with base 50 defining its lateral limits. As indicated above, base 50 may be directly adhered to the distribution manifold or may be positioned and adhered using the drape of the wound dressing. The reduced pressure adapter 22 is positioned on distribution manifold such that the aperture 53 (not seen in this view) of base 50 is in direct contact with the distribution manifold. In the view shown in FIG. 4, primary lumen interface 64 extends centrally out from conduit housing 62 and is surrounded by aperture 66. Conduits extend through the material of reduced pressure adapter 22 between the tubing interfaces and recessed region 54, as described above. The elbow region 68 redirects fluid flow from the wound dressing positioned beneath reduced pressure adapter 22 to an angle associated with interface 64 in a manner that allows the system to be placed on the wound dressing and be maintained close to the wound dressing surface.

FIG. 5 is an end view of the same structure shown in FIG. 4 with the configuration of elbow region 68 and the internal configuration of conduit housing 62 more clearly shown. In this view, the same components associated with adhering reduced pressure adapter 22 to the wound dressing are disclosed. Base 50 and aperture 54 are positioned as indicated in FIG. 4. Conduit housing 62 is shown as it would be positioned to receive a section of tubing for connection to the balance of the system of the present invention.

Internal to conduit housing 62 are primary lumen interface 64 and ancillary lumen interfaces 48 and 49. Ancillary lumen interfaces 48 and 49 align with the corresponding lumens in the delivery tubing by placing the primary lumen in the tubing over the primary lumen interface 64. The structure of one embodiment of multi-lumen tubing used in conjunction with the improved reduced pressure adapter structure of the present invention is described in more detail below.

FIG. 6 provides essentially the same view of reduced pressure adapter 22 as that of FIG. 4 but from the opposite side. Structurally, the elements shown are the same as those shown and described with FIG. 4, which is indicative of the lateral (and to an extent, radial) symmetry of the connector. Unless otherwise indicated, the materials used to construct the improved connector of the present invention may be selected from a number of materials known in the art that provide the necessary flexibility and comfort to the patient while maintaining sufficient rigidity or resilience to maintain the open lumens that are integral to the reduced pressure adapter function.

Figure 7:
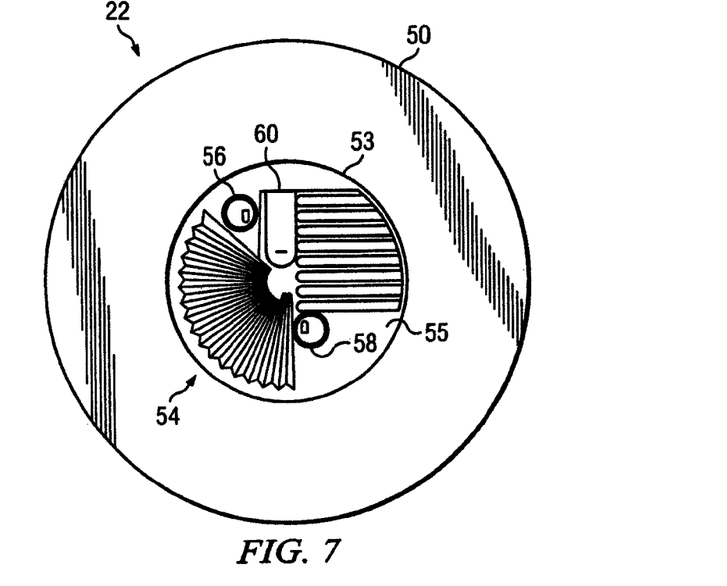
FIG. 7 is a plan view of the underside (open side) of the improved reduced pressure adapter of FIG. 2, the underside configured according to a first exemplary embodiment of the present invention.

FIG. 7 provides a plan view (from below) of reduced pressure adapter 22 and clarifies the structure and function of the various features and elements within recessed region 54 that serve to preference liquids and other non-gaseous fluids away from the ancillary ports 56, 58. In this view, base 50 is shown surrounding the edge of recessed region 54. Ancillary ports 56 and 58 are shown positioned as indicated, with associated conduits extending internally from ports 56 and 58 to ancillary lumen interfaces (hidden and not shown in this view). Primary port 60 can be seen centrally located within aperture 54. The primary conduit extends (hidden and not shown in this view) from primary port 60 through primary lumen interface 64. The specific structures within recessed region 54 that serve to conduct liquid into the primary conduit, and thereby allow the ancillary conduits to remain unobstructed are described in more detail below with respect to FIG. 9.

Figure 8:
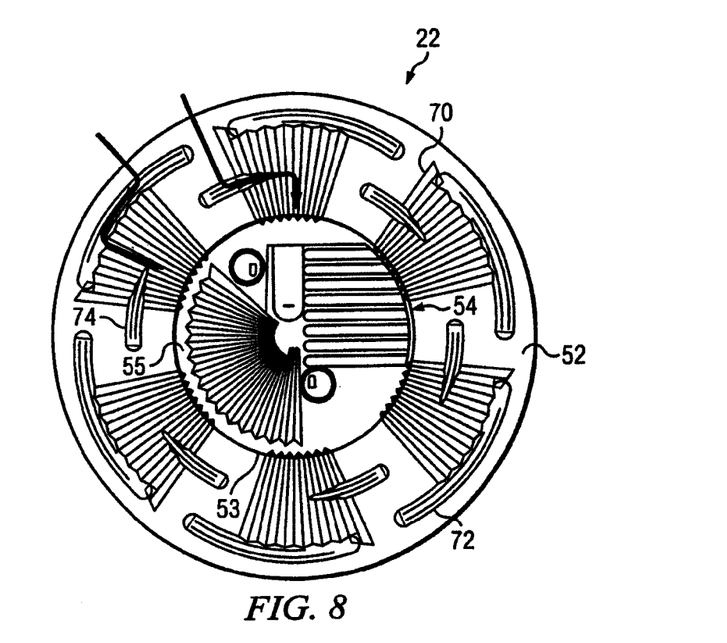
FIG. 8 is a plan view of the underside (open side) of the improved reduced pressure adapter of FIG. 2, the underside configured according to another exemplary embodiment of the present invention.

FIG. 8 shows an alternate exemplary embodiment of the base associated with the reduced pressure adapter of the present invention. In this view (the same perspective as that of FIG. 7) added features to the underside surface of alternate base 52 are shown. These features, molded into the structure of base 52, include base serrated guide channels 70, perimeter collection channels 72, and intermediate collection channels 74. The objective of these channels is to direct liquid away from the two ancillary measurement ports 56, 58 and into the primary port 60. Base serrated guide channels 70 are positioned and oriented on base 50 to directly capture and channel at least half of the liquids being drawn into the reduced pressure adapter, and indirectly channel a major portion of the balance of the liquids being drawn in. The spaced, radially-oriented arrangement of base serrated guide channels 70 funnels liquids away from the ancillary ports and into the primary port. In addition, perimeter collection channels 72 and intermediate collection channels 74 redirect the flow of liquids that are being drawn in between the radially-oriented guide channels 70 into the guide channels 70 and away from the ancillary ports. An example of this redirected flow is shown in FIG. 8 with bolded flow indication arrows.

Figure 9:
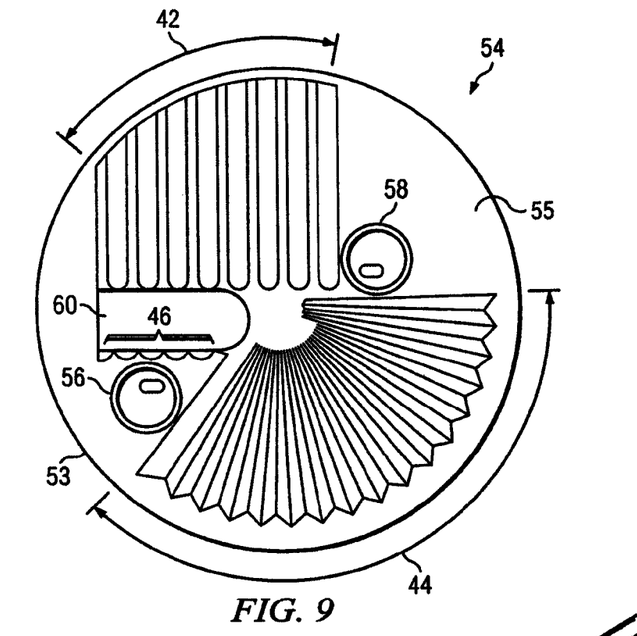
FIG. 9 is a detailed view of a recessed region of the reduced pressure adapter of FIGS. 7 and 8.

Reference is now made to FIG. 9 for a more detailed description of the features and elements contained within the recessed region of conduit housing 62. These features are positioned on the entry surface 55 of the recessed region 54 and are structured to preference liquids and other non-gaseous exudates away from the ancillary ports 56, 58 and into the primary port 60. In this view, primary port 60 is shown centrally positioned within recessed region 54 and extending from the central location to one side of recessed region 54. Ancillary ports 56 and 58 are likewise disclosed in this view, positioned to either side of the central location of primary port 60. In this view, ancillary ports 56 and 58 are circular openings (each with raised circumferential edges) that extend toward a drainage point that opens into an internal conduit extending to the associated ancillary lumen interface (not shown). The openings of the conduits can be seen within the confines of ancillary ports 56 and 58.

Four basic features within the structure shown in FIG. 9 are positioned to preference liquid into the primary port 60 of the reduced pressure adapter 22. The first such structure is simply the placement of the ancillary ports 56 and 58 near the perimeter of the aperture 53 at a level that is close to the surface of the distribution manifold when the reduced pressure adapter 22 is positioned thereon. In other words, when the reduced pressure adapter 22 is positioned on the wound dressing, the ancillary ports 56 and 58 are in contact, or are nearly in contact, with the surface of the distribution manifold. In this manner, the likelihood of splashed or agitated liquid being directed into these ports is minimized.

The remaining three features that direct liquids into the primary port are structural serrated channels formed on various portions of the entry surface 55 of recessed region 54. A first linear serrated channel section 42 is positioned in association with the approximately half circle section of recessed region 54 that is associated with ancillary port 58. The material that comprises the ceiling of this section of recessed region 54 covers and contains the conduit that extends between ancillary port 58 and its interface (not shown). This ceiling or wall is configured with an array of serrated channels or striations that directs liquids that fall upon this surface towards the primary port at the center of the recessed region 54. Any liquids that are drawn into the opening and fall upon this portion of the entry surface 55 would be channeled directly into primary port 60, rather than being directed into ancillary port 58.

A similar configuration is constructed in an approximately one-third circular radial serrated channel section 44. Insofar as no internal conduit is contained within this section of the recessed region 54, the serrated channels in section 44 may extend deeper and more directly to the primary port 60. These radial serrated channels are directed from the perimeter of aperture 54 towards the apex of the recessed region 54 that drains into primary port 60. These radial striations or channels extend from a radius adjacent ancillary port 58 radially around approximately one-third of the circle to a radius adjacent ancillary port 56. Any liquids that fall upon this portion of the recessed region 54 will be directed centrally to primary port 60, rather than being conducted to either of the ancillary ports.

Finally, the wall section that supports ancillary port 56 at the point at which the ancillary port 56 overhangs primary port 60 is structured with serrated or striated channels 46 that extend downward (upward in the normal positioning of the connector) from the opening of ancillary port 56 towards the opening of primary port 60.

As described above, the various internal features and elements of the recessed region 54 are structured to draw liquid from most points within the recessed region 54 towards the centrally located primary port 60. Only liquid that enters directly into ancillary port 56 or 58 would likely be drawing into an ancillary lumen. Insofar as little or no suction is occurring at these ports, this structure greatly reduces the likelihood of obstructions in the form of liquid or material blockages in an ancillary lumen.

Reduced Pressure Delivery Tube

Figure 10:
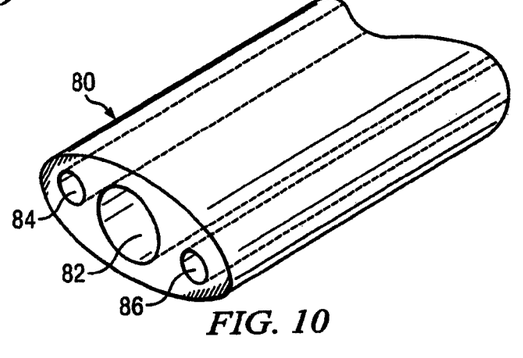
FIG. 10 is a perspective view of an open end of an improved reduced pressure delivery tube according to an exemplary embodiment of the present invention.
Figure 11:
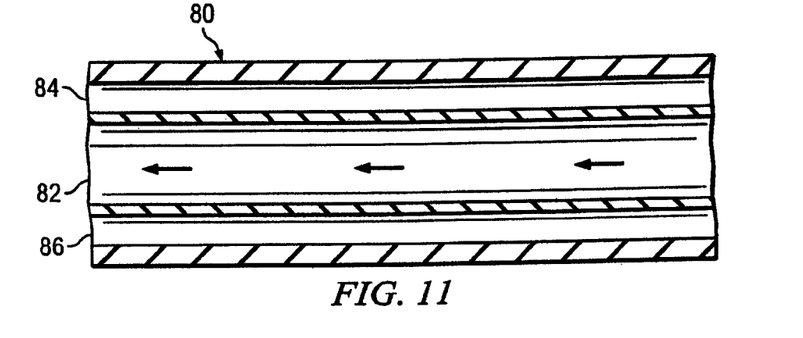
FIG. 11 is a longitudinal cross-sectional view of the improved reduced pressure delivery tube of FIG. 10.

Reference is now made to FIGS. 10 and 11 for a detailed description of the structure of an improved reduced pressure delivery tube 80 operable in association with the system of an exemplary embodiment of the present invention. The reduced pressure delivery tube 80 preferably includes a primary central lumen 82 and ancillary lumens 84 and 86. Ancillary lumens 84 and 86 are generally used for taking pressure measurements. In FIG. 11, fluid flow designated by the block arrows is shown as it would be directed through primary lumen 82 while ancillary lumens 84 and 86 remain generally free of liquid or any non-gaseous matter. The cross-sectional perspectives shown in both FIGS. 10 and 11 disclose the relative cross-sectional diameters of the primary lumen 82 as compared with the ancillary lumens 84 and 86. Delivery device 80 has an oval cross-section, which optimizes flexibility without allowing for the collapse of any of the described lumens. This cross-sectional shape also orients the ancillary lumens 84 and 86 so that the lumens align appropriately with the interfaces on the improved reduced pressure adapter described above.

Dynamic Method of Measuring Wound Pressure

The system of the present invention also includes an improved and dynamic method of measuring the wound pressure that overcomes problems inherent with current reduced pressure wound treatment control systems. Various methods have been developed in the art to control the operation of reduced pressure wound treatment products and systems to insure that the wound pressure is maintained and that the therapy is safe by effective operation of the prescribed regimens. Currently, wound pressure is measured with the outer lumen or lumens of a multi-lumen tube that are commoned together and connected to one pressure sensor. This structure can suffer certain problems if liquid enters the lumens or they become blocked. If such liquid intrusion or blockages occur, the system can become unstable and alarms or indicators related to pressure become unreliable. Various mechanical remedies for these problems have been attempted and some have been partially successful. Ultimately, however, a system such as described in the prior art will be challenged with liquid in the control lumen unless there is a physical barrier placed against the ingress of liquid into the measurement lumen(s). One goal of the present invention is a system that is more reliable and more robust when challenged with extremes of therapy, as compared to current single sensor measurement lumen systems.

Figure 12:
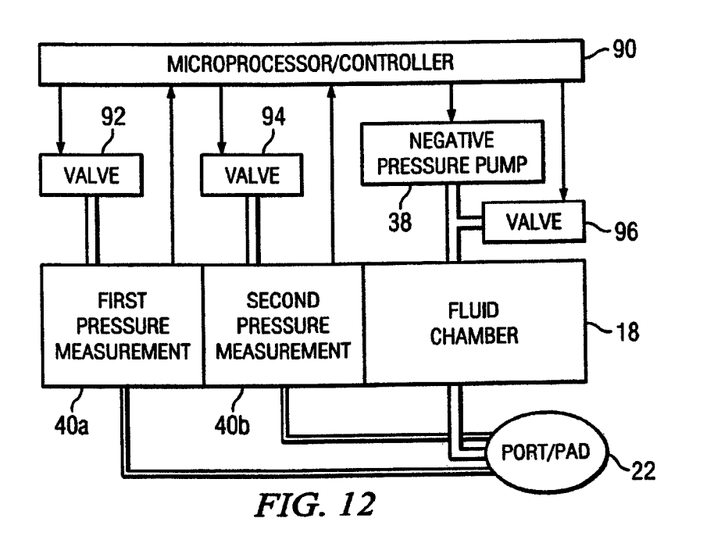
FIG. 12 is a schematic block diagram illustrating the arrangement and functionality of a reduced pressure system according to an exemplary embodiment of the present invention.

Reference is made to FIG. 12 wherein the system of an exemplary embodiment of the present invention and the functional relationship of its components are disclosed. The system incorporates two wound pressure sensors 40a and 40b in the system instrumentation that extend separately (through discrete lumens or conduits) from the instrumentation to the reduced pressure adapter and are not commoned until the discrete lumens combine at the interface of the reduced pressure adapter and the distribution manifold. As indicated above, the reduced pressure adapter incorporates two separate pressure sensing ports as well as the fluid path through fluid chamber 18 to the reduced pressure pump 38 in the system instrumentation. Inside the system instrumentation, each of the ancillary measurement lumen conduits is fitted with a solenoid valve 92 and 94 which will relieve pressure to the wound at the end of therapy, during intermittent therapy, or if required to clear blockages. These valves, as well as a similar valve associated with the reduced pressure source 38, are controlled by microprocessor/controller 90. Microprocessor/controller 90 likewise controls the operation of reduced pressure pump 38 and receives data from first and second pressure measurement devices 40*a* and 40*b*. The microprocessor/controller 90 is programmed to monitor the wound pressure through the two readings associated with the two ancillary lumen paths. In instances where liquid enters one of the lumens, the liquid will cause a delay in the pressure change response time of that lumen versus the clear lumen. As the blockage becomes more acute so will the delay. When a delay is detected, the system will control the wound pressure according to that of the open lumen and will try to clear the liquid from the blocked lumen by opening the appropriate valve to atmosphere. The preferred programming will try to clear the blockage in this manner several times. If the system is not successful in clearing the blockage, the programming will, from that point on, ignore the affected lumen and control the system with the remaining clear lumen. The reduced pressure adapter design of the present invention, as described above, is such as to maximize the chances of having at least one clear ancillary measurement lumen at any given time.

Reduced Pressure Adapter with Rotating Function

Currently, reduced pressure adapters in RPWT systems typically allow for the effective connection of reduced pressure wound therapy to the wound, but do not allow for the tube connection point to be repositioned (for example, in the event that the patient is susceptible to skin breakdown) or for a situation where the user has incorrectly positioned the reduced pressure adapter (for example, in the event that the reduced pressure adapter is facing in the wrong direction). In such instances, the user must remove and discard the reduced pressure adapter, and in some instances the drape, which causes discomfort and is a nuisance to the patient and user as well as an additional cost. Providing a rotation or swivel function to the reduced pressure adapter enables repositioning the tube without having to remove and relocate the reduced pressure adapter. This ability assists in any situation where the tubing requires relocation to avoid tissue damage. One goal of the present invention is to provide a reduced pressure adapter structure that allows for easy relocation of the tubing without removing and relocating the reduced pressure adapter or the wound dressing.

Figure 13:
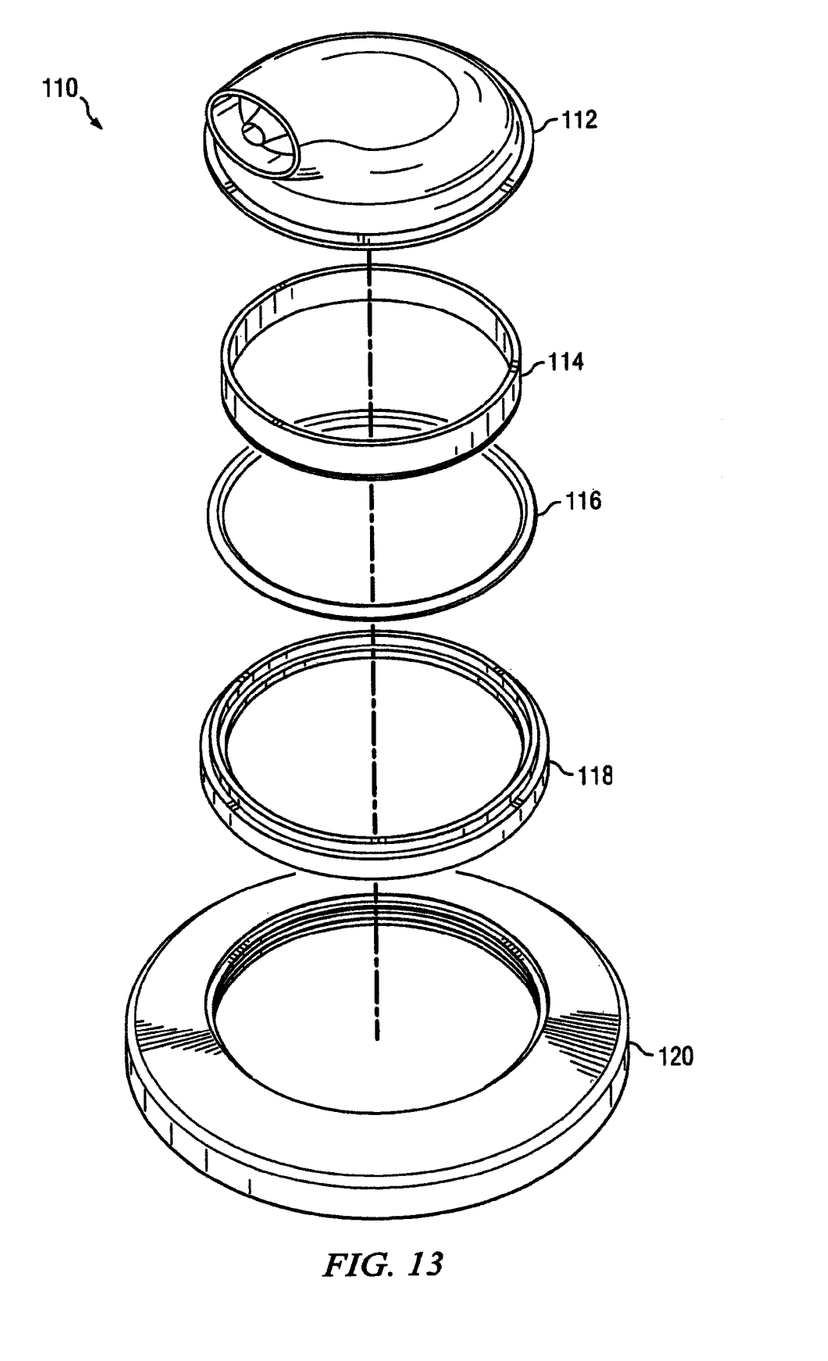
FIG. 13 is an exploded perspective view of an improved reduced pressure adapter according to an exemplary embodiment of the present invention, the reduced pressure adapter incorporating elements that provide rotational functionality.
Figure 14:
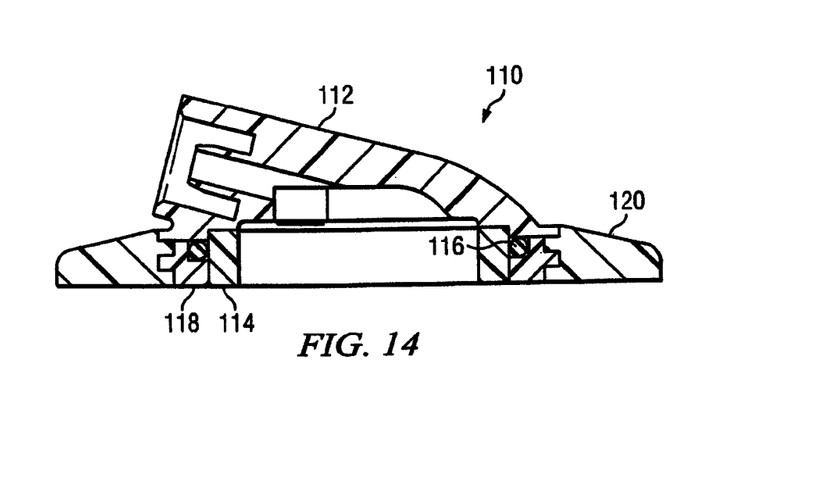
FIG. 14 is a cross-sectional view of the reduced pressure adapter of FIG. 13.

Reference is made to FIGS. 13 and 14 for a description of the configuration of an alternate preferred embodiment of the reduced pressure adapter structure. The reduced pressure adapter 110 shown in FIG. 13 employs a hard plastic inner core that forms a bearing surface to enable a rubber o-ring to seal against it and also to enable the bearing surface to slide past with relatively low friction. Bonded to the hard plastic inner core is a soft thermoplastic or elastomeric polymer that acts as a protective and cushioning cover. FIGS. 13 and 14 show the various circular ring components that go together to make up the swivel connection of the present invention. A top rotating PVC component 112 covers a top ABS insert ring 114 which itself is surrounded by a rubber o-ring 116. A bottom ABS insert ring 118 is shown that holds o-ring 116 captive between it and the top ABS insert 114. Each of these rings is then fitted within the bottom PVC ring 120 which comes into contact with the base of the reduced pressure adapter and/or with the wound dressing itself.

The internal features and elements associated with the reduced pressure adapter as described above in conjunction with a non-rotating embodiment are equally applicable here and may be integrated into the inside structure of top rotating PVC component 112 by direct molding of the component or by positioning a molded insert into a shell to for rotating component 112. In any event, the same benefits of the liquid preferencing structures surrounding the lumen ports described above are obtainable with the rotating functionality of the alternate embodiment described.

FIG. 14 discloses the same components mentioned above as they would be assembled and thereby shows in clearer detail the manner in which the components interlock and rotate with or against each other. In this view, the captive o-ring 116 is also shown to provide a proper seal for the internal reduced pressure chamber formed by the reduced pressure adapter 110. In this view it is also clear how the internal features and elements in the port opening may be appropriately positioned on the underside of top PVC component 112 to serve the function of preferencing liquid to the primary conduit as described above.

Reduced Pressure Adapter with Microorganism Indication

Current reduced pressure treatment systems do not generally alert the caregiver to the presence of microorganisms in wound dressings. Many of these microorganisms can be significant factors in controlling infection at the wound site. One goal of the present invention is to provide a system that will alert the caregiver to significant levels of key microorganisms under the classification of aerobic, non-aerobic, gram positive and gram negative. The response or indication is in the form of color patterns discretely reflecting the four classifications mentioned above.

Figure 15:
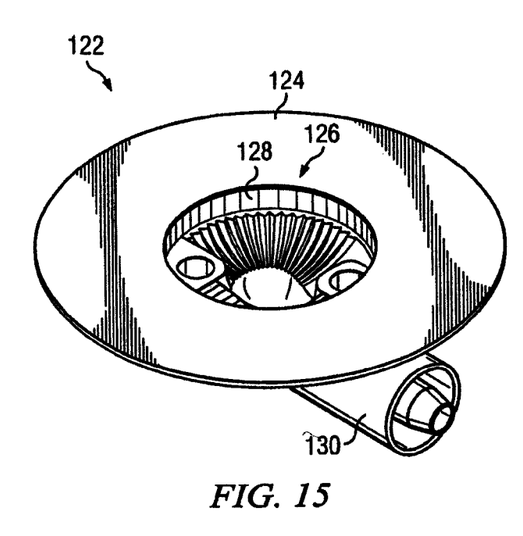
FIG. 15 is a bottom perspective view of a reduced pressure adapter having panels sensitive to the presence of microorganisms according to an exemplary embodiment of the present invention.
Figure 16:
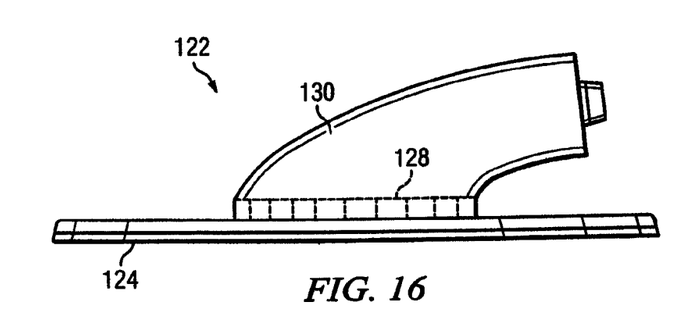
FIG. 16 is a side view of the reduced pressure adapter of FIG. 15 in which the panels are visible through transparent or translucent side walls of the reduced pressure adapter.

A volatile organic compound (VOC) sensitive strip mounted on the reduced pressure adapter or its associated drape is utilized in certain embodiments. When exposed to the targeted VOC known to form in the presence of certain microorganisms, a color pattern becomes apparent and thereby identifies the type of microorganism present in the wound fluid. Referencing FIGS. 15 and 16, a reduced pressure adapter 122 includes a base 124 and a conduit housing 130 similar to that described previously with reference to FIGS. 2-9. The positioning of a VOC sensitive panel 128 in a recessed region 126 of the conduit housing 130 is shown. In FIG. 16, it can be seen that given the translucent or transparent character of the material from which the reduced pressure adapter 122 is constructed, the VOC sensitive panel 128 can be visually inspected even from the exterior while the reduced pressure adapter 122 is in place with base 124 in position against the distribution manifold of the wound dressing. The preferable positioning of this VOC sensitive panel 128 is therefore within the recessed region 126 near the periphery of the recessed region 126 as shown. FIG. 15 shows more clearly the placement of this VOC sensitive panel within the recessed region 126 where it is constantly exposed to the fluid materials being drawn from the wound. Alternate placements of the panels are possible as long as sufficient exposure to wound fluids exists.

It should be apparent from the foregoing that an invention having significant advantages has been provided. While the invention is shown in only a few of its forms, it is not just limited but is susceptible to various changes and modifications without departing from the spirit thereof.

We claim:

1. An apparatus for providing reduced-pressure to a tissue site through a primary lumen, the apparatus comprising:
   a reduced-pressure source; and
   a controller configured to:

operate the reduced-pressure source to change pressure in the primary lumen;

measure pressure through a first measurement lumen and a second measurement lumen, each of the first measurement lumen and the second measurement lumen having openings near the tissue site;

monitor a response time of pressure measured through the first measurement lumen and the second measurement lumen to the pressure change in the primary lumen; and open one or more of the first measurement lumen and the second measurement lumen to a pressure greater than the pressure in the primary lumen if the response time indicates a delayed response.

2. The apparatus of claim 1, further comprising:

an adapter coupled to primary lumen, the first measurement lumen, and the second measurement lumen, the adapter comprising channels configured to direct liquid away from the first measurement lumen and the second measurement lumen.

3. The apparatus of claim 2, wherein the adapter comprises:

a housing having an entry surface;

a primary conduit through the housing coupled to the primary lumen and terminating on the entry surface;

a first ancillary conduit through the housing coupled to the first measurement lumen and terminating on the entry surface; and a second ancillary conduit through the housing coupled to the second measurement lumen and terminating on the entry surface.

4. The apparatus of claim 3, further comprising:

a base attached to the housing; and guide channels on the base.

5. The apparatus of claim 3, further comprising:

a base attached to the housing; and radial guide channels on the base adapted to direct liquid from a periphery of the base away from the first ancillary conduit and the second ancillary conduit.

6. The apparatus of claim 3, further comprising a base attached to the housing, wherein the housing is rotatable about the base.

* * * * *